US00PP24316P3

(12) United States Plant Patent
Dulcich et al.

(10) Patent No.: US PP24,316 P3
(45) Date of Patent: Mar. 18, 2014

(54) GRAPE VINE PLANT DENOMINATED 'JPD-001'

(50) Latin Name: *Vitis vinifera*
Varietal Denomination: JPD-001

(75) Inventors: Jakov P. Dulcich, Delano, CA (US); Nick P. Dulcich, Bakersfield, CA (US); Peter Dulcich, Bakersfield, CA (US)

(73) Assignee: Jakov Dulcich and Sons, LLC, McFarland, CA (US)

( * ) Notice: Subject to any disclaimer, the term of this patent is extended or adjusted under 35 U.S.C. 154(b) by 57 days.

(21) Appl. No.: 13/573,085

(22) Filed: Aug. 20, 2012

(65) Prior Publication Data

US 2013/0198918 P1 Aug. 1, 2013

Related U.S. Application Data

(60) Provisional application No. 61/593,400, filed on Feb. 1, 2012.

(51) Int. Cl.
*A01H 5/00* (2006.01)

(52) U.S. Cl.
USPC ..... Plt./207

(58) Field of Classification Search
USPC ..... Plt./207
See application file for complete search history.

*Primary Examiner* — Annette Para
(74) *Attorney, Agent, or Firm* — Jondle Plant Sciences Division of Swanson & Bratschun, L.L.C.

(57) ABSTRACT

A new and distinct variety of grapevine denominated 'JPD-001', which is characterized by its large natural berry size, increased responsiveness to berry size augmentation, and lack of a noticeable seed trace, is disclosed.

4 Drawing Sheets

RELATED APPLICATIONS

The present Application claims priority of U.S. Provisional Patent Application No. 61/593,400, entitled "Improved *Vitis vinifera* Variety," and filed on Feb. 1, 2012, and which is incorporated herein by reference in its entirety.

STATEMENT REGARDING FEDERALLY SPONSORED RESEARCH OR DEVELOPMENT

Not Applicable.

BACKGROUND OF THE INVENTION

The present invention relates to a new and distinct variety of grapevine, *Vitis vinifera,* which is hereinafter denominated by the variety name 'JPD-001'. More specifically, the invention relates to a grapevine that produces fruit maturing for commercial harvesting and shipment around August 20, in the San Joaquin Valley of Central Calif. The fruit is naturally large and responsive to berry size augmentation treatments. There is no lignified seed trace, and the berries exhibit excellent crispness and a skin not prone to cracking.

The grapevine of the present invention originated from the white, seedless variety, Sheehan-Genetics 10-418 (unpatented). In the spring of 2002, Sheehan-Genetics 10-418 was grafted onto 2-A Thompson Seedless in a variety plot owned by Jakov P. Dulcich and Sons, near McFarland, Calif. The plant that resulted from this grafting was grown from 2002 until 2006, at which time asexual one-bud cuttings of plants resulting from the Sheehan-Genetics 10-418/2-A Thompson Seedless graft were selected from this vineyard and grafted upon a variety known as Crimson at another Jakov P. Dulcich and Sons varietal plot near Delano, Calif. In January, 2010, select samples from this plot exhibiting characteristics desired for what would become JPD-001 were propagated by one-bud asexual cuttings and grafted onto Red Globe (U.S. Plant Pat. No. 4,787) in a variety plot near McFarland, Calif. Resulting plants harvested in 2011 were stable, unique, and distinguishable from the parent plant material. The stability of the resulting plants was demonstrated again in 2012, with additional production of the new variety. These resulting plants are the subject of this plant patent application.

SUMMARY OF THE INVENTION

A new grape vine, denominated JPD-001, is of *Vitis vinifera* parentage. JPD-001 is a large berry-size, white, seedless grape maturing for harvest in approximately the third week of August in the San Joaquin Valley of Central Calif. JPD-001 is distinguished from its parent cultivar, Sheehan-Genetics 10-418, in that it has a much larger natural berry size, crisper texture, and lacks a noticeable seed trace. The lack of a noticeable seed trace is due to the fact that the aborted seed does not lignify, and is aborted much earlier in development and maturity as compared to the parent variety. The present variety also exhibits a heightened response to berry size augmentation treatments.

BRIEF DESCRIPTION OF THE ILLUSTRATIONS

The illustrations of the grapevine of the present invention are color photographs showing the following:

DETAILED DESCRIPTION OF THE INVENTION

Figure 1:
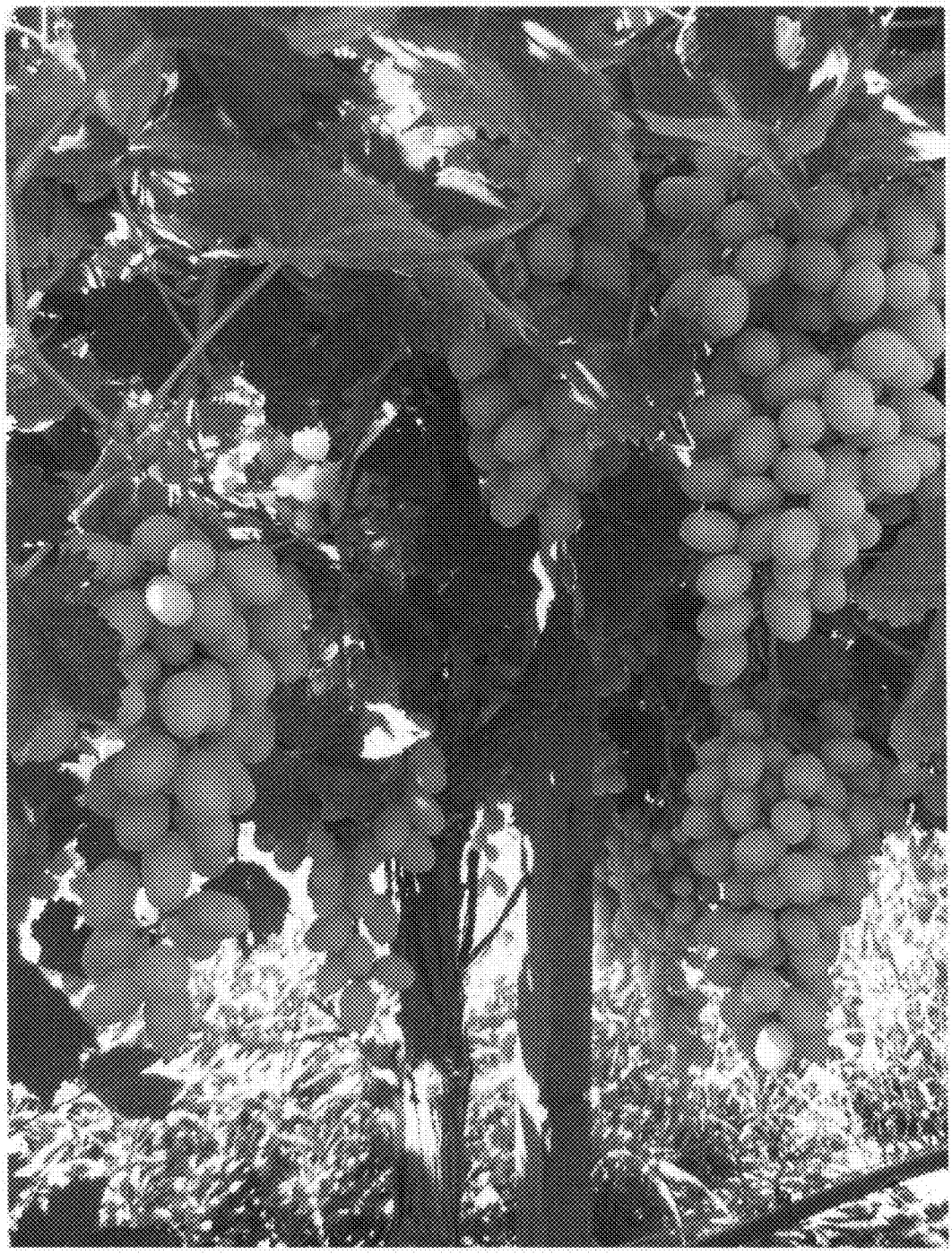
FIG. 1 shows the new variety growing on a trellis in the field.
Figure 2:
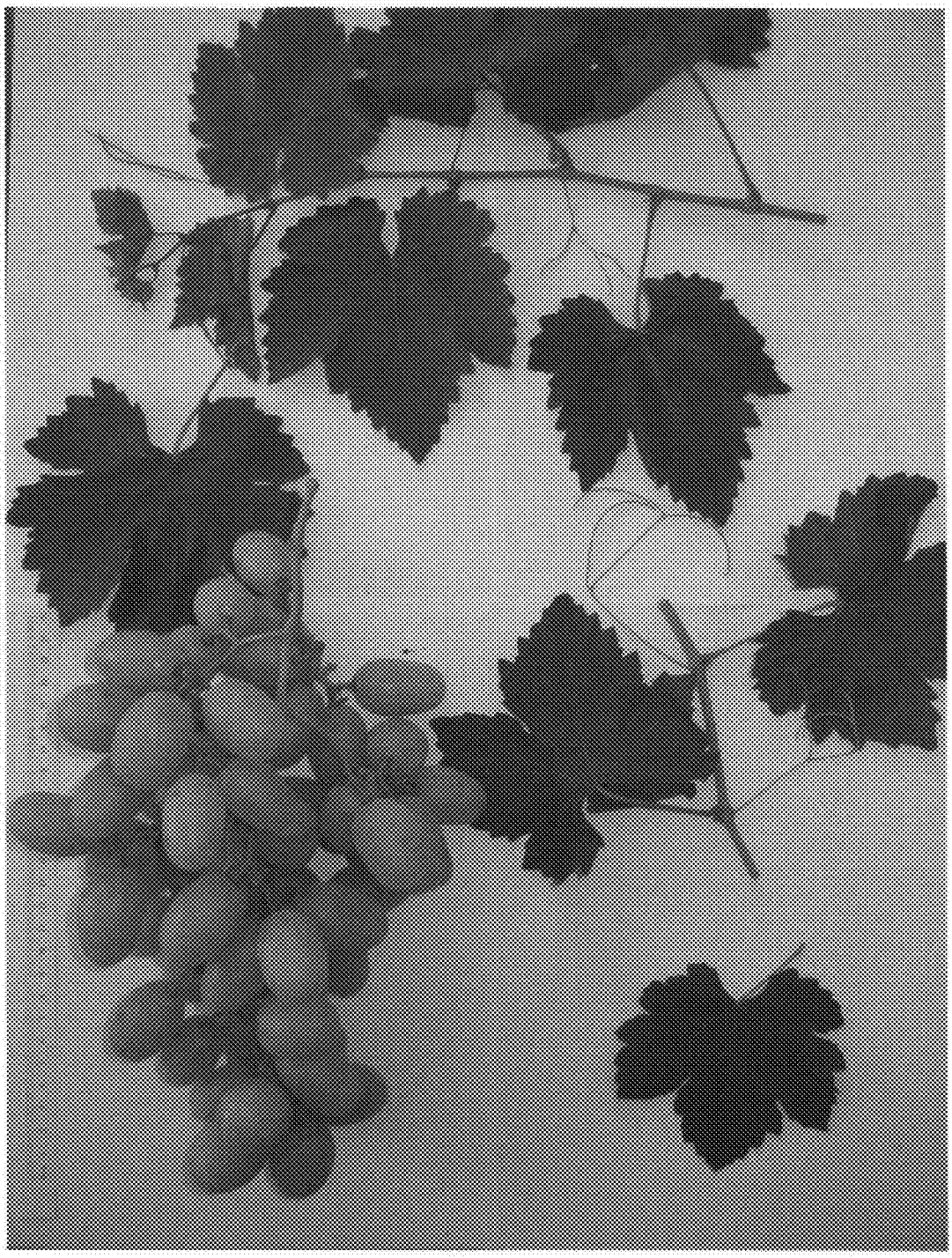
FIG. 2 shows growing tips, leaves, and a berry cluster of the new variety.
Figure 3:
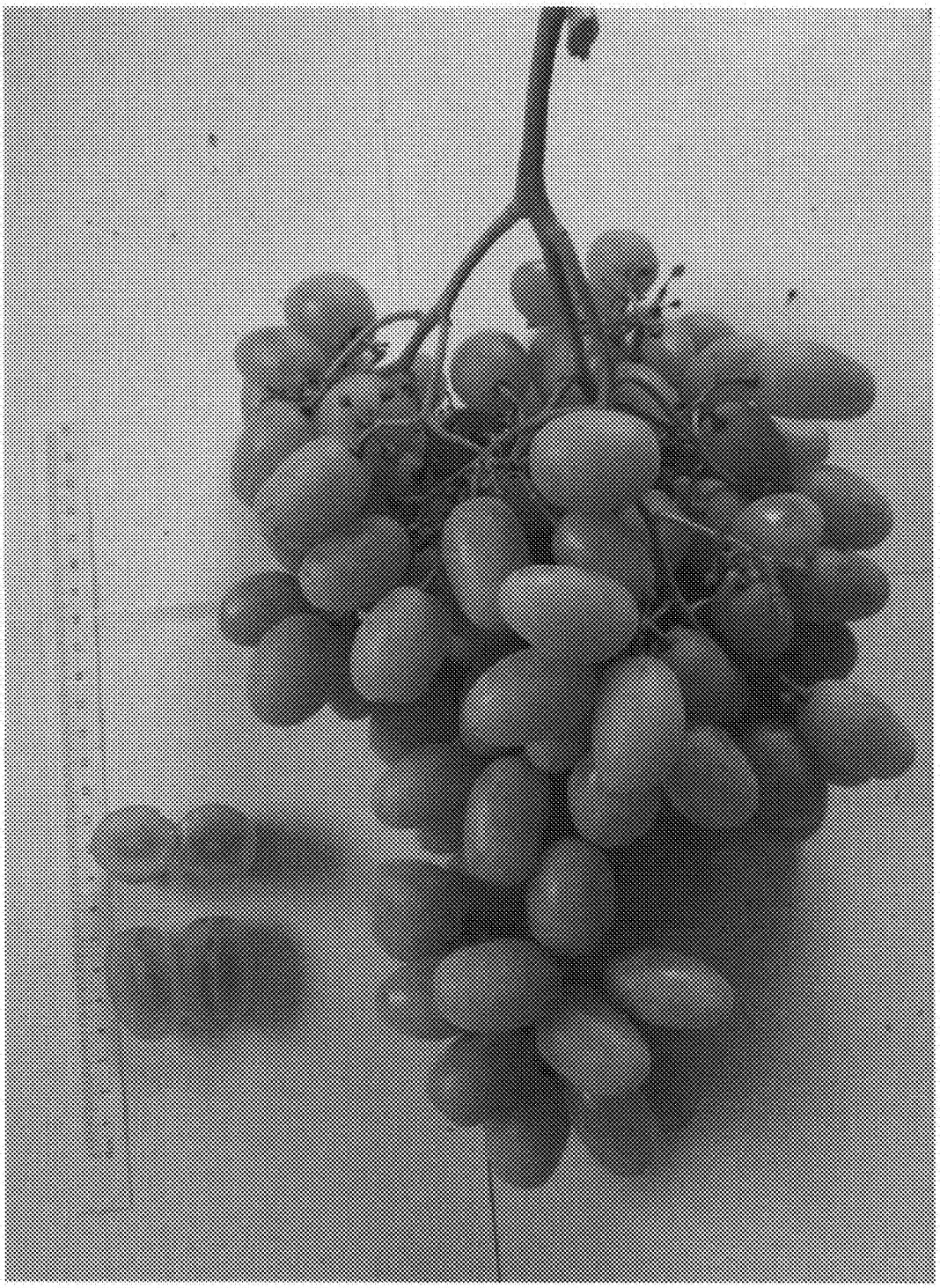
FIG. 3 shows a berry cluster of the new variety, as well as cross-sections of the berries thereof. A measurement of berry size is also provided.
Figure 4:
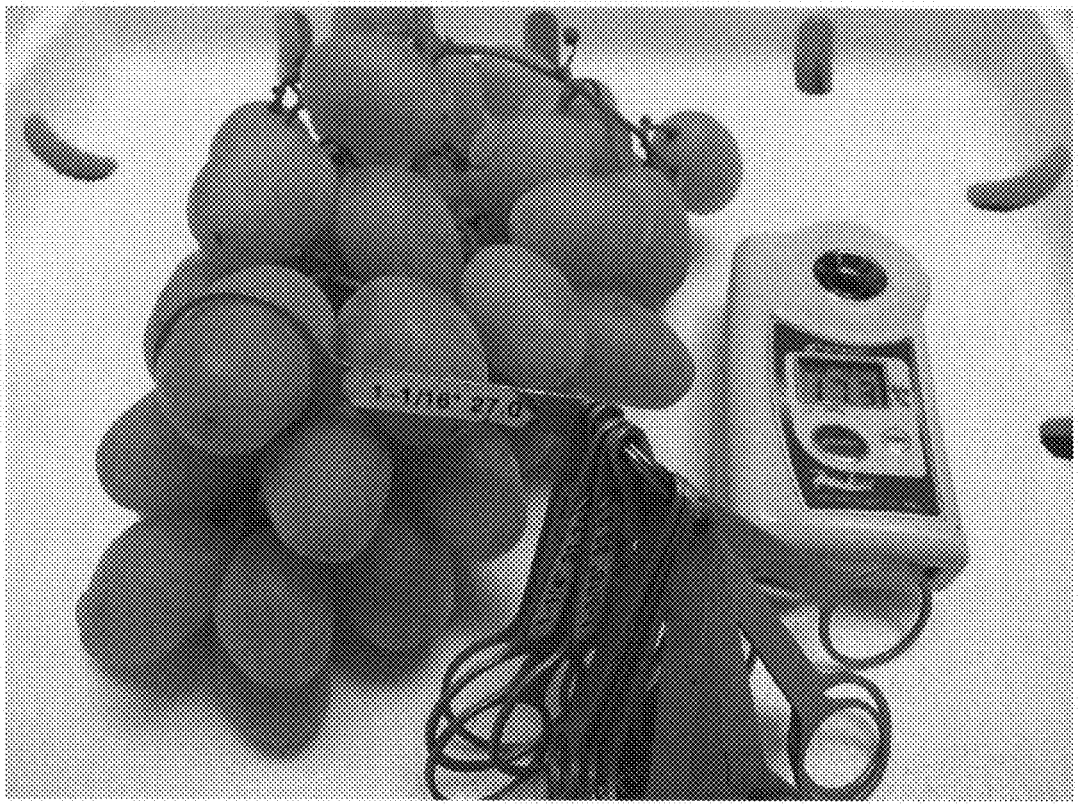
FIG. 4 shows a berry cluster of the new variety and provides a measurement of berry size.

The following is a detailed description of plants in the new variety, JPD-001, grown outdoors near McFarland, Calif., on their own rootstock. The color-terminology used herein is in accordance with The Royal Horticultural Society Colour Code.

JPD-001 is a large berry-size, white, seedless grape maturing for harvest in approximately the third week of August in the San Joaquin Valley of Central Calif.

BOTANICAL DESCRIPTIONS

*Vineyard.*—The vineyard is trained to a quadrilateral cordon on a wood trellis. The approximate height of the trellis is 114 cm with cordons resting at approximately 112 cm. The width between the cordons is approximately 56 cm.

*Vigor.*—Moderately vigorous.

*Growing season.*—April 1 through December 1.

*Productive capacity.*—Good.

Trunk characteristics:

*Size.*—Circumference of 16.5 cm and length of 76 cm from graft union to the cordons.

*Surface texture.*—Rough and shaggy.

*Color of bark.*—(One year or older wood) Gry/G 197-B.

*Cane length.*—1.65 meters.

*Mature/lignified cane color.*—Gry/B N199-D.

*Mature/lignified cane texture.*—Smooth.

*Internode length.*—8 to 10.5 cm.

Branch characteristics:

*Size.*—102 cm in length and 11 cm in circumference.

*Surface texture.*—Slightly tough and shaggy.

*Color.*—(One year old wood) Gry/G 197-B.

*Lenticels.*—0.

Leaves/shoots:

*Size.*—12 to 17 cm.

*Density.*—Moderately dense.

*Form.*—Pentagonal.

*Leaf base.*—Sagittate.

*Texture.*—Upper: Smooth. Lower: Glabrous.

*Color.*—Upper: G 141-B. Lower: G 138-A.

*Leaf vein.*—Color: Y/G 144-B. Thickness: 1.5 to 2 mm. Presence of anthocyanin: Absent.

*Leaf margin.*—Serrated/toothed; slightly undulating.

*Glands.*—Absent.

*Petiole.*—Length: 9 to 11 cm. Thickness: 2 to 4 cm. Erect Hairs on Petiole: Absent. Color: Y/G 144A but with streaks of Gry/R 180-A on side exposed to sun.

*Petiole sinus.*—General shape: Open (ovate).

*Stem glands.*—Absent.

*Stipules.*—Absent.

*Lobes.*—5.

*Teeth.*—Serration length: 0.33 to 1.5 mm; width 0.5 to 1.0 mm. Ratio of length/width: about 1:1.

*Size.*—Large; approximately 18 cm in length at full bloom.

*Shape.*—Long, conical.

*Number borne per shoot.*—One or two.

*Number borne per vine.*—45 to 55.

Flowers:

*General.*—Flower sex: Perfect.

*Flower buds.*—Size: 5 to 7 mm in width and 7 to 8 mm in length. Shape: Triangular. Fruitfulness: Good.

*Flowers.*—Pedicle length: 3 mm. Calyptra color: G 134-A. Ovary: length 2 mm; width 1.5 mm; color G 135-B. Pistil: length 1.5 mm. Anthers: length 0.5 mm; color Y 6-C. Filament: length 1.0 mm; color G 142-C.

*Date of visible berries.*—Approximately May 14.

Fruit:

*Maturity.*—Ripening approximately August 27.

*Solids.*—17.5 to 18.0 brix at desired maturity.

*Acids.*—5.0 to 7.5 TA.

*Sugar/acid ratio.*—2.5:1 to 3.5:1.

*Seeds* (*number, characteristics*).—Two aborted, non-lignified seeds due to embryo abortion.

*Capstem.*—Normal size; color Y/G 145-A.

*Berry weight.*—Average weight; large natural berry size, around 6 g to 7 g; with size augmentation, berry weight increases to around 9 g to 15 g.

*Juice color.*—Y/G 145-B.

*Cluster.*—Large, loose, conical cluster with an average weight of 2 to 3 lbs.

*Stem size* (*general characteristics*).—Strong stem; not prone to breaking, with average thickness.

*Berry size* (*number/bunch*).—Large natural berry size of around 19 mm; with size augmentation treatments, berry size increases to 23 mm to 28 mm.

*Skin.*—Berry skin is of average thickness, and not prone to cracking.

*Seed trace.*—Slight trace of non-lignified seed due to embryo abortion.

*Flesh color.*—Y/G 149-D; very nice eating quality and crunchy texture. Flavor and aroma similar to Thompson Seedless, but with much crisper texture.

*Use.*—Table.

Although the new variety of grapevine described herein possesses the described characteristics noted above as a result of the growing conditions prevailing in or around McFarland, in the Central San Joaquin Valley of Calif., United States of America, it is to be understood that variations of the usual magnitude and characteristics incident to changes in growing conditions, training, irrigation, fertilization, pruning, pest control, climatic variation, and the like, are to be expected.

Having thus described the preferred embodiment of the invention, what is claimed as new and desired to be protected by Letters Patent includes the following:

1. A new and distinct variety of grapevine plant, denominated 'JPD-001', substantially as shown and described herein.

* * * * *